United States Patent
Sezi et al.

[11] Patent Number: 5,998,662
[45] Date of Patent: Dec. 7, 1999

[54] O-AMINO (THIO) PHENOLCARBOXYLIC ACIDS AND THEIR PREPARATION

[75] Inventors: Recai Sezi, Röttenbach; Michael Keitmann, Weisendorf, both of Germany

[73] Assignee: Siemens Aktiengesellschaft, Munich, Germany

[21] Appl. No.: 09/160,875

[22] Filed: Sep. 25, 1998

[30] Foreign Application Priority Data

Sep. 24, 1997 [DE] Germany .............. 197 42 193

[51] Int. Cl.$^6$ .................................. C07C 229/00
[52] U.S. Cl. ............. 562/457; 562/433; 562/441
[58] Field of Search ................. 562/441, 433, 562/457

[56] References Cited

U.S. PATENT DOCUMENTS 4,910,282  3/1990  Abraham et al. ............. 528/185

FOREIGN PATENT DOCUMENTS 0023662   5/1983   European Pat. Off. .
0264678   9/1991   European Pat. Off. .
811758    4/1959   United Kingdom .
1283476   4/1971   United Kingdom .

*Primary Examiner*—Alan L. Rotman
*Assistant Examiner*—Rita Desai
*Attorney, Agent, or Firm*—Herbert L. Lerner; Laurence A. Greenberg

[57] ABSTRACT

The invention relates to novel o-aminophenolcarboxylic acids, and o-aminothiophenolcarboxylic acids of the following structure:

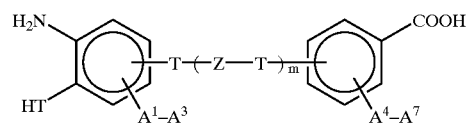

where $A^1$ to $A^7$ are—independently of one another—H, F, $CH_3$, $CF_3$, $OCH_3$, $OCF_3$, $CH_2CH_3$, $CF_2CF_3$, $OCH_2CH_3$ or $OCF_2CF_3$, where at least one of the radicals $A^1$ to $A^3$ must be F or an F-containing group; T is O or S, and m is 0 or 1; and Z is a carbocyclic or heterocyclic aromatic radical.

10 Claims, No Drawings

O-AMINO (THIO) PHENOLCARBOXYLIC ACIDS AND THEIR PREPARATION

BACKGROUND OF THE INVENTION

FIELD OF THE INVENTION

The invention relates to novel o-aminophenolcarboxylic acids and o-aminothiophenolcarboxylic acids, which are also jointly abbreviated to o-amino(thio)phenol-carboxylic acids, and to a process for their preparation.

o-aminophenolcarboxylic acids are needed, in particular, for the preparation of high-temperature-stable polymers, such as polybenzoxazoles (PBOs) and their precursors. Compared with the preparation of polybenzoxazoles or PBO precursors from bis-o-aminophenols and dicarboxylic acids, the use of o-aminophenol-carboxylic acids has significant advantages. For example, an o-aminophenolcarboxylic acid can be reacted with itself, i.e. a second monomer is not absolutely necessary for the polymerization. Thus, purity monitoring and storage are simplified, and in addition, the stoichiometry is predefined, i.e. errors in the calculations or weighing-out of the reactants, as can occur in the reaction of bis-o-aminophenols with dicarboxylic acids, are excluded if o-aminophenol-carboxylic acids are used. Furthermore, the nature of the monomer used has a strong effect on the property profile of the PBO precursor or polybenzoxazole prepared therewith. For example, not only the thermal, electrical and mechanical behavior, but also the solubility and hydrolysis stability and numerous other properties of the polymer are greatly affected by the monomer used in the preparation.

PBO precursors in the form of a photosensitive composition can be structured inexpensively by direct methods, i.e. without an auxiliary resist. Compared with other dielectrics which can be photostructured directly, such as polyimide (PI) and benzocyclobutene (BCB), PBO precursors offer the advantage of positive structurability and aqueous-alkaline development (see EP 0 023 662 B1 and EP 0 264 678 B1). To this end, the PBO precursors used must be substantially transparent at the exposure wavelength and sufficiently soluble in the developer, which preferably contains no metal ions. Like polyimides, polybenzoxazoles also have the major advantage that they—compared with the cyclized final product—as readily soluble precursors, can be applied to a substrate and then cyclized, during which the solubility and thus the sensitivity to solvents and other process chemicals decreases greatly.

Besides good solubility of the precursors, advantages for the use of polybenzoxazoles in microelectronics are low moisture absorption and a good planarization capacity. Production of components using a dielectric which produces good planarization allows expensive polishing procedures (chemical mechanical polishing, CMP) to be avoided.

o-aminophenolcarboxylic acids are disclosed, for example, in GB 811,758 and GB 1,283,476. In PBO films produced from the known monomers, the water absorption in boiling water after 24 h is 0.77%. No mention is made of the planarization behavior of the polymers produced after cyclization on the substrate or their suitability as base polymers for compositions which can be photo-structured positively.

SUMMARY OF THE INVENTION

The object of the invention is to provide o-aminophenolcarboxylic acids and o-aminothiophenolcarboxylic acids which are suitable for the preparation of polymers which satisfy the greatly increased demands of microelectronics. The o-amino(thio)phenolcarboxylic acids should, in particular, enable the preparation of readily soluble polymer precursors which, after cyclization on a substrate, give polybenzoxazoles or polybenzothiazoles of low moisture absorption and high degree of planarization.

This is achieved in accordance with the invention by o-aminophenolcarboxylic acids and o-aminothiophenol-carboxylic acids of the following structure:

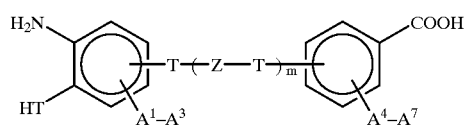

in which $A^1$ to $A^7$ are—independently of one another—H, F, $CH_3$, $CF_3$, $OCH_3$, $OCF_3$, $CH_2CH_3$, $CF_2CF_3$, $OCH_2CH_3$ or $OCF_2CF_3$, where at least one of the radicals $A^1$ to $A^3$ must be F or an F-containing group;

T is O or S, m is 0 or 1;

and Z is one of the following carbocyclic or heterocyclic aromatic radicals:

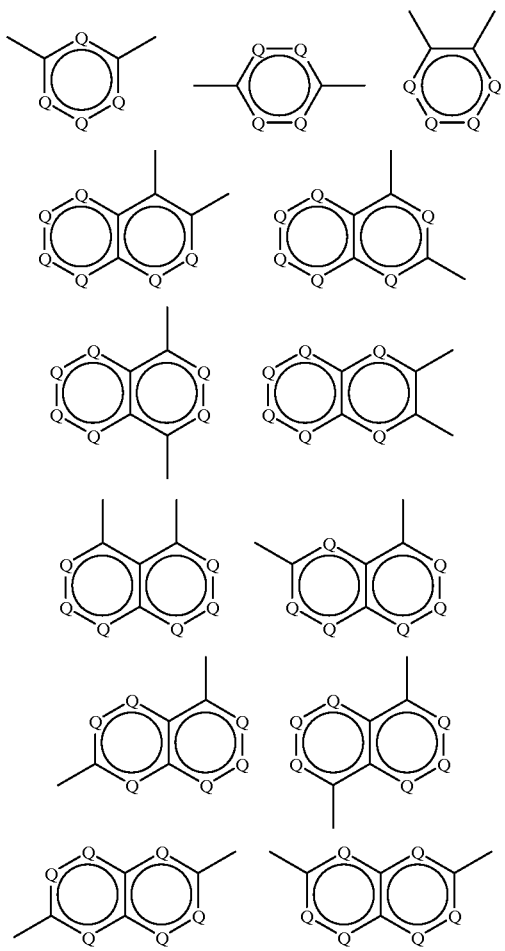

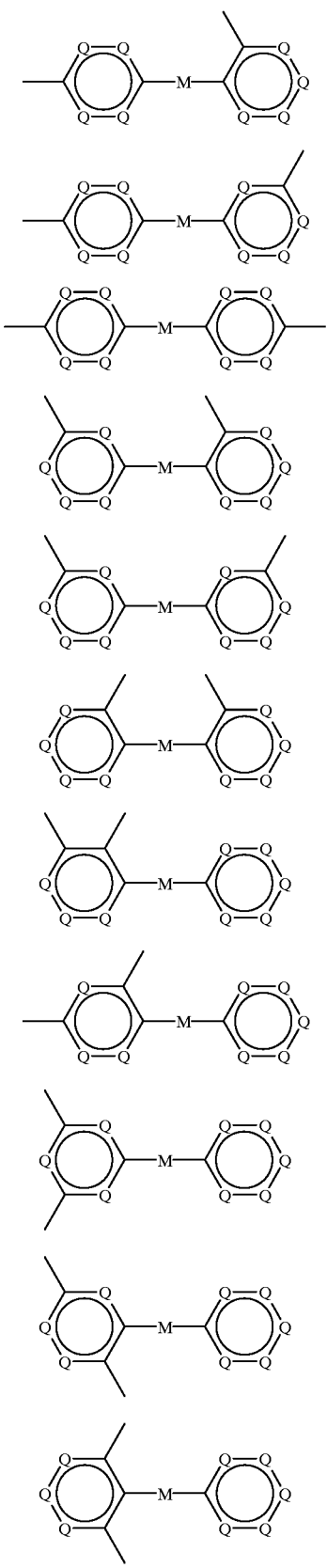

or

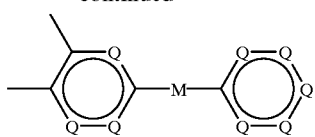

or wherein Q=C—A or N, and A=H, F, $(CH_2)_pCH_3$, $(CF_2)_pCF_3$, $O(CH_2)_pCH_3$, $O(CF_2)_pCF_3$, $CO(CH_2)_pCH_3$, $CO(CF_2)_pCF_3$, where p=0 to 8 (linear or branched chain), $OC(CH_3)_3$, $OC(CF_3)_3$, $C_6H_5$, $C_6F_5$, $OC_6H_5$, $OC_6F_5$, cyclopentyl, perfluorocyclopentyl, cyclohexyl or perfluorocyclohexyl, where, in the isolated aromatic rings, a maximum of 3 N-atoms may be present per ring and only 2 N-atoms may be adjacent, and, in the fused ring systems, a maximum of 2 N-atoms may be present per ring, M=a single bond, $(CH_2)_n$, $(CF_2)_n$, $CH(CH_3)$, $CH(CF_3)$, $CF(CH_3)$, $CF(CF_3)$, $C(CH_3)_2$, $C(CF_3)_2$, $CH(C_6H_5)$, $CH(C_6F_5)$, $CF(C_6H_5)$, $CF(C_6F_5)$, $C(CH_3)(C_6H_5)$, $C(CH_3)(C_6F_5)$, $C(CF_3)(C_6H_5)$, $C(CF_3)(C_6F_5)$, $C(C_6H_5)_2$, $C(C_6F_5)_2$, CO, $SO_2$,

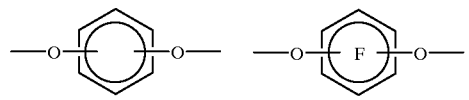

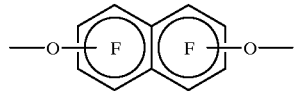

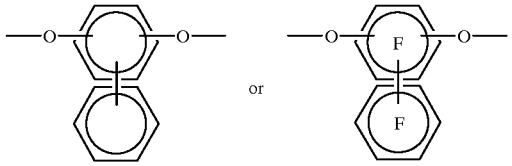

or

The novel compounds have, for example, the following structure:

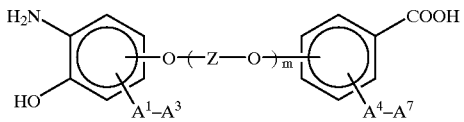

In compounds of this type, the ether bridges are apparently responsible for the good solubility and the good planarization properties of the polymer precursors prepared therewith. By the way, the characterization "$A^1$–$A^3$" and "$A^4$–$A^7$" in the structural formula means that the aminophenyl groups contain radicals $A^1$, $A^2$ and $A^3$, and radicals $A^4$, $A^5$, $A^6$ and $A^7$ respectively.

The o-amino(thio)phenolcarboxylic acids can be prepared by (a) reacting a halogen-containing nitro compound of the structure

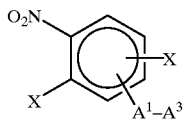

with a hydroxy or mercapto compound of the structure

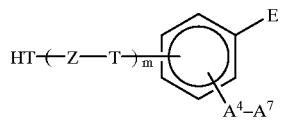

in the presence of at least a stoichiometric amount of a base, or with an alkali metal salt of the hydroxy or mercapto compound, in a solvent at a temperature between −10 and 80° C., where X is a halogen atom, E is CN or $COOR^1$, where $R^1$=alkyl (having 1 to 5 carbon atoms), phenyl or benzyl, and $A^1$ to $A^7$, T and Z are as defined above; and (b) reducing and hydrolyzing the resultant nitro compound to the amino compound.

In this synthesis, which is very economical, firstly a nitro compound containing at least two halogen atoms, one of which is in the o-position to the nitro group, is thus reacted with a hydroxy or mercapto compound containing an ester or nitrile group. The resultant o-nitro(thio)phenol is then reduced to the corresponding amino compound, and the ester or nitrile group is hydrolyzed to the carboxyl group.

The hydroxy or mercapto compound is an aromatic or substituted aromatic compound. Suitable compounds for the reaction with the aromatic nitro compound are in principle all those in which the hydroxyl or mercapto group has adequate nucleophilicity.

Alternatively, the o-amino(thio)phenolcarboxylic acids can also be prepared by (a) reacting a halogen compound of the structure

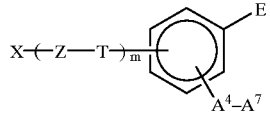

with a nitrophenol or nitrothiophenol (abbreviated to "nitro (thio)phenol") of the structure

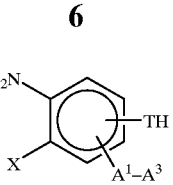

in the presence of at least a stoichiometric amount of a base, or with an alkali metal salt of the nitro(thio)phenol, in a solvent at a temperature between −10 and 80° C., where X is a halogen atom, E is CN or $COOR^1$, where $R^1$=alkyl (having 1 to 5 carbon atoms), phenyl or benzyl, and $A^1$ to $A^7$, T and Z are as defined above; and (b) reducing and hydrolyzing the resultant nitro compound to the amino compound.

In this synthesis, which is likewise very economical, a halogen-containing ester or a corresponding nitrile is thus reacted with a nitro(thio)phenol containing a halogen atom in the o-position to the nitro group. The resultant nitro compound is then reduced to the corresponding amino compound, and the ester or nitrile group is hydrolyzed to the carboxyl group.

DESCRIPTION OF PREFERRED EMBODIMENTS

The reaction between the hydroxy or mercapto compound and the nitro compound, in which an ether or thioether bridge is formed, is carried out in the presence of a base. This base is preferably a carbonate or hydrogen-carbonate of an alkali metal or alkaline earth metal, such as sodium carbonate or potassium carbonate. For the (thio)ether formation and for replacement of the halogen atom (in the o-position to the nitro group) by a hydroxyl or mercapto group, at least the stoichiometric amount of the base is necessary in each case.

It may also be advantageous to use an organic base containing a tertiary N-atom, for example triethylamine or pyridine. In this case, the addition of water is necessary. The hydroxy or mercapto compound can also be replaced by a corresponding alkali metal salt, for example the potassium salt.

A reaction temperature in the range from −10 to 80° C. has proven suitable. Temperatures $\leq 80°$ C. are preferred owing to the greater selectivity of the reaction. It is advantageous here initially to maintain a temperature of $\leq 25°$ C. for some time, for example for about 16 hours, during which the reaction of the nitro compound with the hydroxy or mercapto compound takes place. The reaction is then continued at elevated temperature, i.e. $\geq 40°$ C.; during this reaction, the replacement of the halogen atom by a hydroxy or mercapto compound and the hydrolysis of the ester or nitrile group takes place. This procedure results in the selective formation of products in which the hydroxyl or mercapto group is in the o-position to the nitro group. In the second step, the temperature can also be <40° C. if the temperature difference to the first step is $\geq 20°$ C.

Suitable solvents are, in particular, dimethylformamide, diethylformamide, dimethylacetamide, dimethyl sulfoxide, N-methylpyrrolidone, γ-butyrolactone, aceto-nitrile, tetrahydrofuran and pyridine. In principle, however, all polar aprotic solvents in which the starting compounds are soluble can be used.

The reduction of the nitro compound can be carried out, for example, by hydrogenation using hydrogen on Pd/C. In principle, however, all the processes which are suitable for reducing the nitro group to the amino group are suitable.

The reduction of the nitro compound and the hydrolysis of the ester or nitrile group can be carried out in two separate process steps, the hydrolysis being carried out, for example, using sulfuric acid; these process steps can be carried out in any desired sequence. In the presence of an ester group, however, the reduction of the nitro group and the hydrolysis preferably are carried out simultaneously, by hydrogenation using hydrogen on Pd/C. Hydrogenation is preferably carried out at temperatures of from 25 to 50° C. Suitable solvents are esters ethers, for example ethyl acetate and tetrahydrofuran.

The polymer precursors prepared from the o-amino(thio)-phenolcarboxylic acids of the invention and having improved properties compared with the prior art are soluble in many organic solvents, such as acetone, cyclohexanone, N-methylpyrrolidone, diethylene glycol mono- or diethyl ether, ethyl lactate and γ-butyrolactone, and in aqueous-alkaline developers containing no metal ions. They are therefore highly suitable as base polymers for dielectrics which can be photo-structured positively and can be developed in aqueous-alkaline media. The precursors can easily be applied to substrates, such as silicon wafers, by spin-coating methods, they form uniform films, and can readily be cyclized on the substrate. A particular advantage of the precursors prepared from these o-amino(thio) phenolcarboxylic acids is their high planarization capacity and low moisture absorption.

The invention will, be illustrated in greater detail below with reference to working examples.

EXAMPLE 1
Preparation of benzyl 4-(4-nitro-3-hydroxy-2,5,6-trifluorophenoxy)benzoate

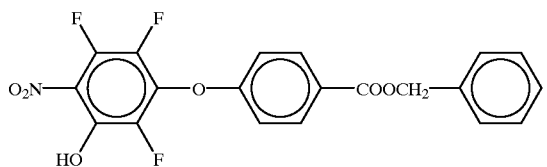

42.6 g of pentafluoronitrobenzene (0.2 mol) are dissolved in 300 ml of N-methylpyrrolidone. After 30 g of potassium carbonate (0.22 mol) have been added, the mixture is cooled to −5° C., and a solution of 45.6 g of benzyl 4-hydroxybenzoate (0.2 mol) in 300 ml of N-methylpyrrolidone is then added drop wise over the course of 30 minutes with stirring. After 1 hour, the reaction temperature is raised to 23° C. for 24 hours, and 800 ml of water and 300 ml of ethyl acetate are then added. The organic phase is separated, washed three times with water and dried over sodium sulphate. The solution is then concentrated in a rotary evaporator until yellow crystals precipitate. The reaction product is washed with petrol ether (boiling range 60–80° C.), collected on a Büchner funnel and dried in a vacuum drying cabinet under nitrogen at 40° C./10 mbar (Yield 89%).

Characterization:
Mass spectrum: molecular peak at 419
Elemental analysis:
Theoretical value (in %): C: 57.3 H:.2.9 N: 3.3
Found (in %) C: 57.5 H: 3.0 N: 3.3
m.p.: 78° C.

EXAMPLE 2
Preparation of 4-(4-amino-3-hydroxy-2,5,6-trifluorophenoxy)benzoic acid

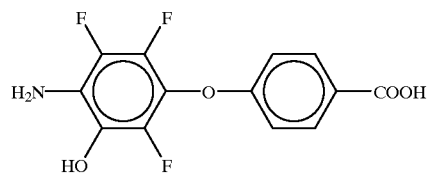

50 g of benzyl 4-(4-nitro-3-hydroxy-2,5,6-trifluorophenoxy)benzoate (0.12 mol) prepared as described in Example 1 are dissolved in 600 ml of a mixture of tetrahydrofuran and ethyl acetate (volume ratio 1:1), and 5 g of Pd/C (palladium/carbon) are added to the solution. The mixture is then hydrogenated at room temperature in an autoclave with vigorous stirring using hydrogen at a pressure of 1 bar; after 3 days, the reaction is terminated. The yellow solution is evaporated to half in a rotary evaporator and left to stand overnight at room temperature, during which the reaction product precipitates in crystalline form. The reaction product is then dried for 48 hours under nitrogen at 40° C./10 mbar in a vacuum drying cabinet (yield: 93%).

Characterization:
Mass spectrum: molecular peak at 299
Elemental analysis:
Theoretical value (in %): C: 52.2 H: 2.7 N: 4.7
Found (in %) C: 52.1 H: 2.7 N: 4.6

EXAMPLE 3
Preparation of 4-(4-benzyloxycarbonylphenoxy) nonafluorobiphenyl

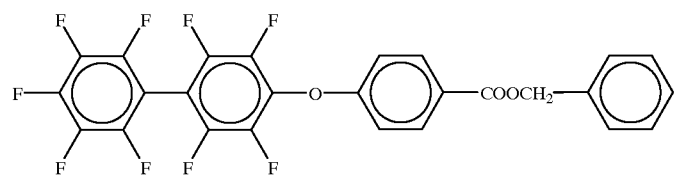

37.6 g of decafluorobiphenyl (0.112 mol) are dissolved in 700 ml of dimethylformamide, and the solution is cooled to −10° C. by means of a cryostat, and a solution of 15 g of potassium 4-benzyloxycarbonylphenoxide (0.056 mol) in 300 ml of dimethylformamide is then added drop wise over the course of 2 hours. After 48 hours at −10° C., the potassium salt has reacted. The dimethylformamide is then removed in a rotary evaporator, and the residue is taken up in a little tetrahydrofuran and filtered via a silica-gel column. The clear solution obtained is evaporated in a rotary evaporator until the reaction product precipitates. The reaction product is then stirred in n-hexane, filtered off via a fluted filter and then dried for 48 hours under nitrogen at 40° C./10 mbar in a vacuum drying cabinet.

Characterization:

Mass spectrum: molecular peak at 542

Elemental analysis:

Theoretical value (in %): C: 57.6 H: 2.0

EXAMPLE 5

Preparation of 4-(4-nitro-3-hydroxy-2,5,6-trifluoro-phenoxy)-4'-(4-benzyloxycarbonylphenoxy)octafluoro-biphenyl

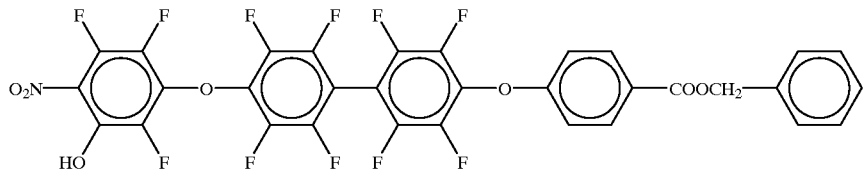

Found (in %) C: 57.5 H: 1.9 m.p.: 120° C.

EXAMPLE 4

Preparation of 4-nitrotetrafluorophenol

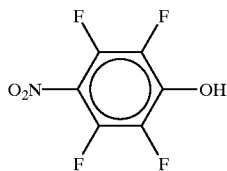

21.3 g of pentafluoronitrobenzene (0.1 mol) are dissolved in 400 ml of dimethyl sulfoxide; a solution of 11.2 g of potassium hydroxide (0.2 mol) in 100 ml of water is added drop wise to this solution with vigorous stirring. After 24 hours at room temperature, the crude product is extracted by shaking with 200 ml of ethyl acetate and 400 ml of water. The organic phase is washed three times with water, dried over sodium sulfate and evaporated to half in a rotary evaporator. The reaction product crystallizes out of the initially viscous solution. The reaction product is then recrystallized from a mixture of n-hexane and dichloromethane (volume ratio 1:1) and then dried for 48 hours under nitrogen at 40° C./10 mbar in a vacuum drying cabinet (yield: 95%).

Characterization:

Mass spectrum: molecular peak at 211

Elemental analysis:

Theoretical value (in %): C: 34.1 H: 0.5 N: 6.6

Found (in %) C: 34.0 H: 0.4 N: 6.7 m.p.: 171° C.

50 g of 4-(4-benzyloxycarbonylphenoxy)nonafluoro-biphenyl (0.092 mol) prepared as described in Example 3 and 19.4 g of 4-nitrotetrafluorophenol (0.092 mol) prepared as described in Example 4 are dissolved in 400 ml of dimethyl sulfoxide. 25 g of potassium carbonate (0.184 mol) are added in portions to the solution. The mixture is then stirred at room temperature for 24 hours and then heated at 60° C. for 24 hours, and 10 g of potassium hydrogencarbonate (0.1 mol) are then added. The reaction solution is then cooled to room temperature and filtered through a fluted filter. The crude product is extracted by shaking with 300 ml of ethyl acetate and 700 ml of water, and the organic phase is washed three times with water and evaporated in a rotary evaporator until the reaction product precipitates. The reaction product is then recrystallized from a mixture of ethyl acetate and n-hexane (volume ratio 1:1) and then dried for 48 hours under nitrogen at 40° C./10 mbar in a vacuum drying cabinet (yield: 92%).

Characterization:

Mass spectrum: molecular peak at 731

Elemental analysis:

Theoretical value (in %): C: 52.5 H: 1.7 N: 1.9

Found (in %) C: 52.7 H: 1.8 N: 1.8

EXAMPLE 6

Preparation of 4-(4-amino-3-hydroxy-2,5,6-trifluoro-phenoxy)-4'-(4-carboxyphenoxy)octafluoro-biphenyl

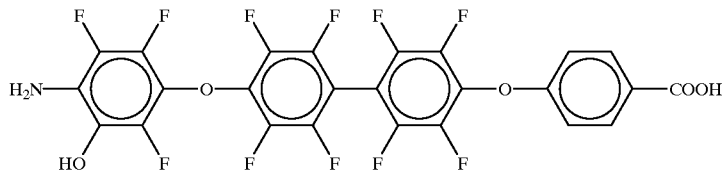

50 g of 4-(4-nitro-3-hydroxy-2,5,6-trifluoro-phenoxy)-4'-(4-benzyloxycarbonylphenoxy)octafluoro-biphenyl (0.069 mol) prepared as described in Example 5 are dissolved in 600 ml of a mixture of tetrahydrofuran and ethyl acetate (volume ratio 1:1), and 5 g of Pd/C (palladium/carbon) are added to the solution. The mixture is then hydrogenated at room temperature in an autoclave with vigorous stirring using hydrogen at a pressure of 1 bar; after 3 days, the reaction is terminated. The orange solution is evaporated to half in a rotary evaporator and left to stand overnight at room temperature, during which the reaction product precipitates out in crystalline form. The reaction product is then dried for 48 hours under nitrogen at 40° C./10 mbar in a vacuum drying cabinet (yield: 93%).

Characterization:
Mass spectrum: molecular peak at 611
Elemental analysis:
Theoretical value (in %): C: 49.1 H: 1.3 N: 2.3
Found (in %) C: 48.9 H: 1.4 N: 2.3

EXAMPLE 7

Preparation of 2-(4-benzyloxycarbonylphenoxy)-3,4,5,6-tetrafluoropyridine

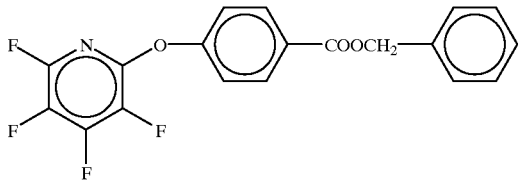

33.8 g of pentafluoropyridine ( 0.2 mol) are dissolved in 500 ml of dimethylformamide, and the solution is cooled to 0° C. by means of a cryostat and a solution of 53.6 g of potassium-4-benzyl-oxycarbonylphenoxide (0.2 mol) in 400 ml of dimethylformamide is then added drop wise over the course of 2 hours. After 24 hours at 0° C., the potassium salt has reacted. The dimethylformamide is then removed in a rotary evaporator, and the residue is taken up in a little tetrahydrofuran and filtered via a silica-gel column. The clear solution obtained is evaporated in a rotary evaporator until the reaction product precipitates out. The reaction product is then stirred in n-hexane, filtered off via a fluted filter and then dried for 48 hours under nitrogen at 40° C./10 mbar in a vacuum drying cabinet (yield: 91%).

Characterization:
Mass spectrum: molecular peak at 377
Elemental analysis:
Theoretical value (in %): C: 60.5 H: 2.9 N: 3.7
Found (in %) C: 60.6 H: 2.9 N: 3.6

EXAMPLE 8

Preparation of 4-(4-nitro-3-hydroxy-2,5,6-trifluoro-phenoxy)-2-(4-benzyloxycarbonylphenoxy)-3,5,6-tri-fluoropyridine

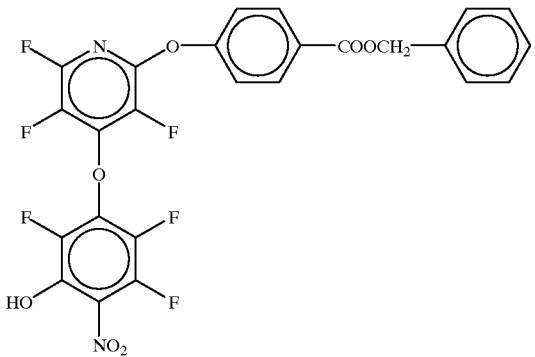

40 g of 2-(4-benzyloxycarbonylphenoxy)-3,4,5,6-tetrafluoropyridine (0.106 mol) prepared as described in Example 7 and 22.4 g of 4-nitrotetrafluorophenol (0.106 mol) prepared as described in Example 4 are dissolved in 400 ml of dimethyl sulfoxide. 30 g of potassium carbonate (0.22 mol) are added in portions to the solution. The mixture is then stirred at room temperature for 24 hours and then heated at 60° C. for 24 hours, and 15 g of potassium hydrogen-carbonate (0.15 mol) are then added. The reaction solution is then cooled to room temperature and filtered through a fluted filter. The crude product is extracted by shaking with 300 ml of ethyl acetate and 700 ml of water, and the organic phase is washed three times with water and evaporated in a rotary evaporator until the reaction product precipitates out. The reaction product is then recrystallized from a mixture of ethyl acetate and n-hexane (volume ratio 1:1) and then dried for 48 hours under nitrogen at 40° C./10 mbar in a vacuum drying cabinet (Yield: 92%).

Characterization:
Mass spectrum: molecular peak at 566
Elemental analysis:
Theoretical value (in %): C: 53.0 H: 2.1 N: 4.9
Found (in %) C: 52.8 H: 2.1 N: 5.0

EXAMPLE 9

Preparation of 4-(4-amino-3-hydroxy-2,5,6-trifluoro-phenoxy)-2-(4-carboxyphenoxy)-3,5,6-trifluoropyridine

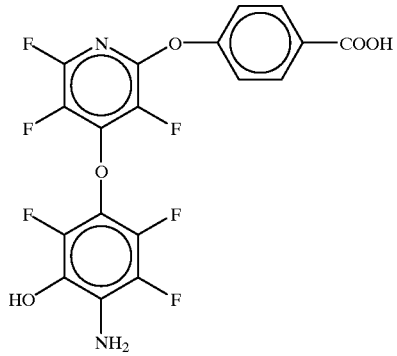

35 g of 4-(4-nitro-3-hydroxy-2,5,6-trifluoro-phenoxy)-2-(4-benzyloxycarbonylphenoxy)-3,5,6-tri-fluoropyridine (0.062 mol) prepared as described in Example 8 are dissolved in 500 ml of a mixture of tetrahydrofuran and ethyl acetate (volume ratio 1:1), and 3.5 g of Pd/C (palladium/carbon) are added to the solution. The mixture is then hydrogenated at room temperature in an autoclave with vigorous stirring using hydrogen at a pressure of 1 bar; after 2 days, the reaction is terminated. The yellow solution is evaporated to half in a rotary evaporator and left to stand overnight at room temperature, during which the reaction product precipitates out in crystalline form. The reaction product is then dried for 48 hours under nitrogen at 40° C./10 mbar in a vacuum drying cabinet (yield: 91%).

Characterization:
Mass spectrum: molecular peak at 446
Elemental analysis:
Theoretical value (in %): C: 48.4 H: 1.8 N: 6.3
Found (in %) C: 48.5 H: 1.7 N: 6.3

We claim:
1. An o-aminophenolcarboxylic acid or a-aminothiophenolcarboxylic acid of the structure

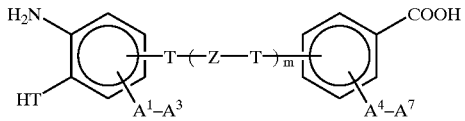

in which
A$^1$ to A$^7$ are—independently of one another—H, F, CH$_3$, CF$_3$, OCH$_3$, OCF$_3$, CH$_2$CH$_3$, CF$_2$CF$_3$, OCH$_2$CH$_3$ or OCF$_2$CF$_3$, where et least one of the radicals A$^1$ to A$^3$ must be F or an F-containing group;

T is O or S, m is 1;

and Z is one of the following carbocyclic aromatic radicals:

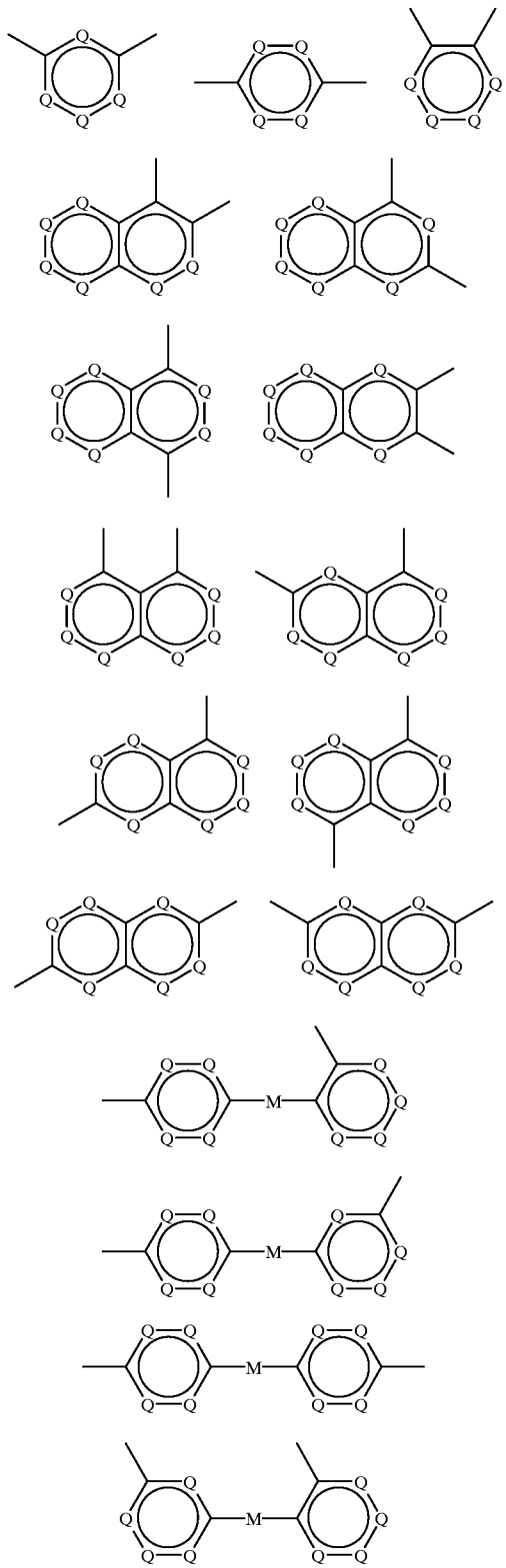

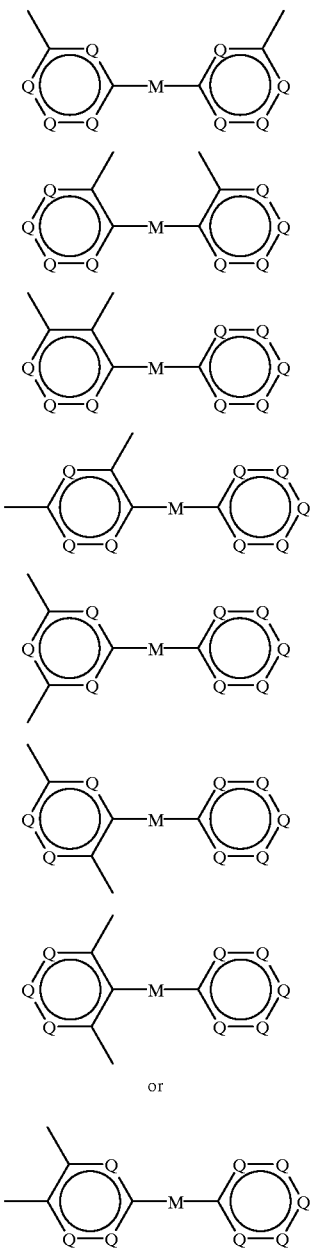

or wherin Q=C—A, and A=H, F, $(CH_2)_p CH_3$, $(CF_2)_p CF_3$, $O(CH_2)_p CH_3$, $O(CF_2)_p CF_3$, $CO(CH_2)_p CH_3$, $CO(CF_2)_p CF_3$, where p=0 to 8 (linear to branched chain), $OC(CH_3)_3$, $OC(CF_3)_3$, $C_6H_5$, $C_6F_5$, $OC_6H_5$, $OC_6F_5$, cyclopentyl, perfuorocyclopentyl, cyclohexyl or perfluorocyclohexyl, M=a single bond, $(CH_2)_n$, $(CF_2)_n$, $CH(CH_3)$, $CH(CF_3)$, $CF(CH_3)$, $CF(CF_3)$, $C(CH_3)_2$, $C(CF_3)_2$, $CH(C_6H_5)$, $CH(C_6F_5)$, $CF(C_6H_5)$, $CF(C_6F_5)$, $C(CH_3)(C_6H_5)$, $C(CH_3)(C_6F_5)$, $C(CF_3)(C_6H_5)$, $C(CF_3)(C_6F_5)$, $C(C_6H_5)_2$, $C(C_6F_3)_2$, CO, $SO_2$,

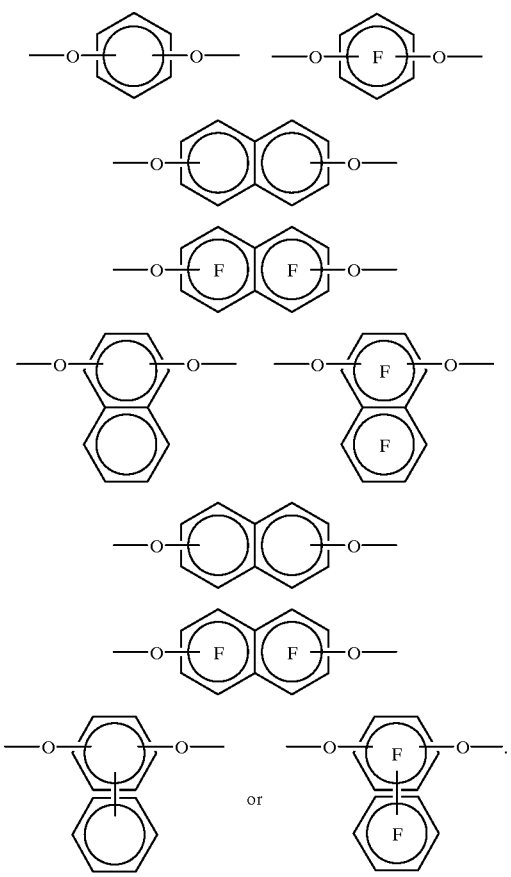

2. An o-aminophenolcarboxylic acid according to claim 1 of the structure

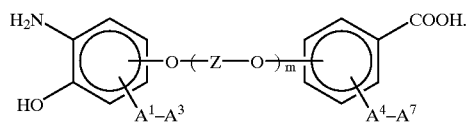

3. An o-aminophenolcarboxylic acid according to claim 2 in which each of $A^1$–$A^3$ is F and each of $A^4$–$A^7$ is H.

4. An o-aminophenolcarboxylic acid according to claim 2 of the structure

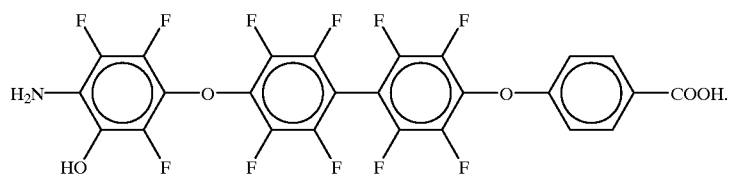

5. A process for the preparation of an o-aminophenolcarboxylic acid or o-aminothiophenolcarboxylic acid as claimed in claim 1, which comprises (a) reacting a halogen-containing nitro compound of the structure

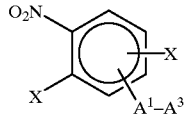

with a hydroxy or mercapto compound of the structure

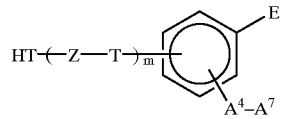

in the presence of at least the stoichiometric amount of a base, or with an alkali metal salt of the hydroxy or mercapto compound, in a solvent at a temperature between −10 and 80° C., where X is a halogen atom, E is CN or COOR$^1$, where R$^1$=alkyl (having 1 to 5 carbon atoms), phenyl or benzyl, and $A^1$ to $A^7$, T and Z are as defined above, and (b) reducing and hydrolyzing the resultant nitro compound to the amino compound.

6. A process for the preparation of an o-aminophenolcarboxylic acid or o-aminothiophenolcarboxylic acid as claimed in claim 1, which comprises (a) reacting a halogen compound of the structure

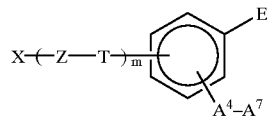

with a nitrophenol or nitrothiophenol of the structure

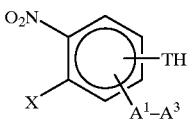

in the presence of at least the stoichiometric amount of a base, or with an alkali metal salt of the nitrophenol or nitrothiophenol, in a solvent at a temperature between −10 and 80° C., where X is a halogen atom, E is CN or COOR$^1$, where R$^1$=alkyl (having 1 to 5 carbon atoms), phenyl or benzyl, and $A^1$ to $A^7$, T and Z are as defined above; and (b) reducing and hydrolyzing the resultant nitro compound to the amino compound.

7. A process as claimed in claim 5 or 6, wherein the base used is a carbonate or hydrogencarbonate of an alkali metal or alkaline earth metal.

8. A process as claimed in claim 5 or 6, wherein an organic base containing a tertiary N-atom is used together with water.

9. A process as claimed in any one of claims 5 to 8, wherein the reduction and, if $E=COOR^1$ the hydrolysis, are carried out by means of hydrogen and are catalyzed by Pd/C.

10. A process as claimed in claim 6 for producing an o-aminophenolcarboxylic acid of the structure

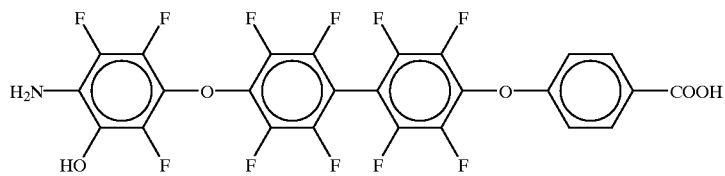

which comprises a) reacting 4-nitrotetrafluorophenol with 4-(4-benzyloxycarbonylphenoxy)-nonafluorobiphenyl in presence of base and b) reducing and hydrolyzing, thereby removing the benzyl group, the resulting nitro compound of the structure

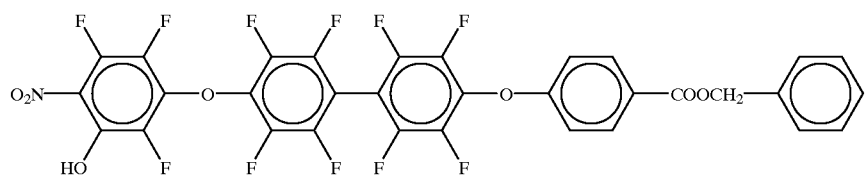

to the amino compound.

* * * * *